(12) United States Patent
Karlsson et al.

(10) Patent No.: US 6,337,394 B2
(45) Date of Patent: *Jan. 8, 2002

(54) COMPOUNDS

(75) Inventors: Olle Karlsson, Mölndal; Marcel Linschoten, Västra Frölunda; Jan-Erik Nyström, Lindome, all of (SE)

(73) Assignee: AstraZeneca AB, Sodertalje (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,143

(22) PCT Filed: Dec. 1, 1998

(86) PCT No.: PCT/SE98/02187

§ 371 Date: Dec. 29, 1998

§ 102(e) Date: Dec. 29, 1998

(87) PCT Pub. No.: WO99/29664

PCT Pub. Date: Jun. 17, 1999

(30) Foreign Application Priority Data

Dec. 5, 1997 (SE) .................................................. 9704543

(51) Int. Cl.[7] ........................ A01N 61/00; A01N 43/04; C07D 345/00; C07D 223/04; C07D 213/00
(52) U.S. Cl. ................................ 540/1; 541/1; 541/44; 541/183; 540/607; 546/1
(58) Field of Search ............................ 514/183, 1, 44; 540/1, 607; 546/1

(56) References Cited

U.S. PATENT DOCUMENTS

| | | | |
|---|---|---|---|
| 4,346,078 A | 8/1982 | Bajusz et al. | 424/177 |
| 4,703,036 A | 10/1987 | Bajusz et al. | 514/18 |
| 5,187,157 A | 2/1993 | Kettner et al. | 514/18 |
| 5,260,307 A | 11/1993 | Ackermann et al. | 514/323 |
| 5,405,854 A | 4/1995 | Ackermann et al. | 514/315 |
| 5,510,369 A | 4/1996 | Lumma et al. | 514/422 |
| 5,559,232 A | 9/1996 | Ackermann et al. | 544/121 |
| 5,561,146 A | 10/1996 | Kim et al. | 514/326 |
| 5,583,146 A | 12/1996 | Kimball et al. | 514/326 |
| 5,602,253 A | 2/1997 | Antonsson et al. | 544/330 |
| 5,614,499 A | 3/1997 | Bylund et al. | 514/19 |
| 5,629,324 A | 5/1997 | Vacca et al. | 514/316 |
| 5,705,487 A | 1/1998 | Ohshima et al. | 514/19 |
| 5,707,966 A | 1/1998 | Schacht et al. | 514/19 |
| 5,710,130 A | 1/1998 | Schacht et al. | 514/19 |
| 5,723,444 A | 3/1998 | Antonsson et al. | 514/19 |
| 5,726,159 A | 3/1998 | Schacht et al. | 514/19 |
| 5,736,521 A | 4/1998 | Bylund et al. | 514/19 |
| 5,741,792 A | 4/1998 | Kimball et al. | 514/237.2 |
| 5,741,799 A | 4/1998 | Kimball et al. | 514/326 |
| 5,744,487 A | 4/1998 | Schacht et al. | 514/326 |
| 5,747,460 A | 5/1998 | Bylund et al. | 514/19 |
| 5,780,631 A | 7/1998 | Antonsson et al. | 546/1 |
| 5,783,563 A | 7/1998 | Antonsson et al. | 514/19 |
| 5,852,051 A | 12/1998 | Bohm et al. | 514/423 |
| 5,856,307 A | 1/1999 | Antonsson et al. | 514/18 |
| 5,914,319 A | 6/1999 | Schacht et al. | 514/19 |
| 5,932,637 A | 8/1999 | Ito et al. | 523/451 |
| 5,939,392 A | 8/1999 | Antonsson et al. | 514/18 |
| 5,955,433 A | 9/1999 | Bylund et al. | 514/19 |
| 5,965,692 A | 10/1999 | Gustafsson et al. | 530/300 |
| 6,030,972 A | 2/2000 | Bohm et al. | 514/257 |

FOREIGN PATENT DOCUMENTS

| | | |
|---|---|---|
| EP | 185 390 | of 0000 |
| EP | 195 212 | 9/1986 |
| EP | 293 881 | 12/1988 |
| EP | 362 002 | 4/1990 |
| EP | 364 344 | 4/1990 |
| EP | 468 231 | 1/1992 |
| EP | 526 877 | 2/1993 |
| EP | 530 167 | 3/1993 |
| EP | 542 525 | 5/1993 |
| EP | 559 046 | 9/1993 |
| EP | 601 459 | 6/1994 |
| EP | 623 596 | 11/1994 |
| EP | 641 779 | 3/1995 |
| EP | 648 780 | 4/1995 |
| EP | 0648780 | * 4/1995 |
| EP | 0 669 317 A1 | 8/1995 |
| EP | 672 658 | 9/1995 |
| EP | 686 642 | 12/1995 |
| WO | 93/11152 | 6/1993 |
| WO | 93/18060 | 9/1993 |
| WO | 94/29336 | 12/1994 |
| WO | 95/23609 | 9/1995 |
| WO | 95/35309 | 12/1995 |

(List continued on next page.)

OTHER PUBLICATIONS

Claesson, Blood Coagul. Fibrinol., vol. 5, p. 411 (1994).
Blomback et al, J. Clin. Lab. Invest., vol. 24, suppl. 107, p. 59 (1969).
Labes et al, Pharmazie, vol. 34 (1979).

Primary Examiner—Jezia Riley
(74) Attorney, Agent, or Firm—Nixon & Vanderhye

(57) ABSTRACT

There is provided compounds of formula I, $$R^1O\text{—}\underset{R^2}{\underset{|}{C}}\text{—}R_x\text{—}\underset{O}{\underset{\|}{C}}\text{—}N\diagup\diagdown Y$$

$$\diagdown \underset{O}{\underset{\|}{C}}\text{—}\underset{H}{\underset{|}{N}}\text{—}(CH_2)_n\text{—}B$$

wherein $R^1$, $R^2$, $R^3$, $R_x$, Y, n and B have meanings given in the description which are useful as competitive inhibitors of trypsin-like proteases, such as thrombin, and in particular in the treatment of conditions where inhibition of thrombin is required (e.g. thrombosis) or as anticoagulants.

9 Claims, No Drawings

FOREIGN PATENT DOCUMENTS

| | | |
|---|---|---|
| WO | 96/03374 | 2/1996 |
| WO | 96/17860 | 6/1996 |
| WO | 96/24609 | 8/1996 |
| WO | 96/25426 | 8/1996 |
| WO | 96/31504 | 10/1996 |
| WO | 96/32110 | 10/1996 |
| WO | 97/02284 | 1/1997 |
| WO | 97/23499 | 7/1997 |
| WO | 97/46577 | 12/1997 |
| WO | 98/01422 | 1/1998 |
| WO | 98/06740 | 2/1998 |
| WO | 98/06741 | 2/1998 |
| WO | 98/57932 | 12/1998 |

\* cited by examiner

COMPOUNDS

FIELD OF THE INVENTION

This invention relates to novel pharmaceutically useful compounds, in particular competitive inhibitors of trypsin-like serine proteases, especially thrombin, their use as medicaments, pharmaceutical compositions containing them and synthetic routes to their production.

1. Background

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

By inhibiting the aggregation of platelets and the formation and crosslinking of fibrin, effective inhibitors of thrombin would therefore be expected to exhibit antithrombotic activity. In addition, antithrombotic activity would be expected to be enhanced by effective inhibition of the positive feedback mechanism.

2. Prior Art

The early development of low molecular weight inhibitors of thrombin has been described by Claesson in Blood Coagul. Fibrinol. (1994) 5, 411.

Blombäck et al. (in J. Clin. Lab. Invest. 24, suppl. 107, 59, (1969)) reported thrombin inhibitors based on the amino acid sequence situated around the cleavage site for the fibrinogen Aα chain. Of the amino acid sequences discussed, these authors suggested the tripeptide sequence Phe-Val-Arg (P9-P2-P1, hereinafter referred to as the P3-P2-P1 sequence) would be the most effective inhibitor.

Thrombin inhibitors based on dipeptidyl derivatives with an α, ω-aminoalkyl guanidine in the P1-position are known from U.S. Pat. No. 4,346,078 and International Patent Application WO 93/11152. Similar, structurally related, dipeptidyl derivatives have also been reported. For example International Patent Application WO 94/29336 discloses compounds with, for example, aminomethyl benzamidines, cyclic aminoalkyl amidines and cyclic aminoalkyl guanidines in the P1-position; European Patent Application 0 648 780, discloses compounds with, for example, cyclic aminoalkyl guanidines in the P1-position.

Thrombin inhibitors based on peptidyl derivatives, also having cyclic aminoalkyl guanidines (e.g. either 3- or 4-aminomethyl-1-amidinopiperidine) in the P1-position are known from European Patent Applications 0 468 231, 0 559 046 and 0 641 779.

Thrombin inhibitors based on tripeptidyl derivatives with arginine aldehyde in the P1-position were first disclosed in European Patent Application 0 185 390.

More recently, arginine aldehyde-based peptidyl derivatives, modified in the P3-position, have been reported.

For example, International Patent Application WO 93/18060 discloses hydroxy acids, European Patent Application 0 526 877 des-amino acids, and European Patent Application 0 542 525 O-methyl mandelic acids in the P3-position.

Inhibitors of serine proteases (e.g. thrombin) based on electrophilic ketones in the P1-position are also known. For example, European Patent Application 0 195 212 discloses peptidyl α-keto esters and amides, European Patent Application 0 362 002 fluoroalkylamide ketones, European Patent Application 0 364 344 α,β,δ-triketocompounds, and European Patent Application 0 530 167 α-alkoxy ketone derivatives of arginine in the P1-position.

Other, structurally different, inhibitors of trypsin-like serine proteases based on C-terminal boronic acid derivatives of arginine and isothiouronium analogues thereof are known from European Patent Application 0 293 881.

More recently, thrombin inhibitors based on peptidyl, and amino acid, derivatives have been disclosed in European Patent Application 0 669 317 and International Patent Applications WO 95/35309, WO 95/23609, WO 94/29336, WO 97/02284, WO 97/46577, WO 98/06740 and WO 98/06741.

However, there remains a need for a effective inhibitors of trypsin-like serine proteases, such as thrombin. There is a particular need for compounds which are both orally bioavailable and selective in inhibiting thrombin over other serine proteases. Compounds which exhibit competitive inhibitory activity towards thrombin would be expected to be especially useful as anticoagulants and therefore in the therapeutic treatment of thrombosis and related disorders.

DISCLOSURE OF THE INVENTION

According to the invention there is provided a compound of formula I,

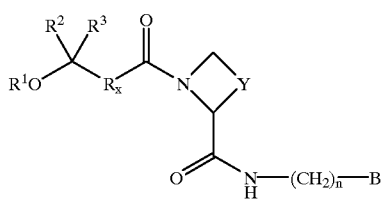

wherein $R^1$ represents H, $C(O)R^{11}$, $SiR^{12}R^{13}R^{14}$ or $C_{1-6}$ alkyl (which latter group is optionally substituted or terminated by one or more substituents selected from $OR^{15}$ or $(CH_2)_q R^{16}$);

$R^{12}$, $R^{13}$ and $R^{14}$ independently represent H, phenyl or $C_{1-6}$ alkyl;

$R^{16}$ represents $C_{1-4}$ alkyl, phenyl, OH, $C(O)OR^{17}$ or $C(O)N(H)R^{18}$;

$R^{18}$ represents H, $C_{1-4}$ alkyl or $CH_2C(O)OR^{19}$;

$R^{15}$ and $R^{17}$ independently represent H, $C_{1-6}$ alkyl or $C_{7-9}$ alkylphenyl;

$R^{11}$ and $R^{19}$ independently represent H or $C_{1-4}$ alkyl; and q represents 0, 1 or 2;

$R^2$ and $R^3$ independently represent H, $C_{1-4}$ alkyl, cyclohexyl or phenyl;

$R_x$ represents a structural fragment of formula IIa, IIb or IIc,

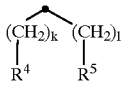
IIa

IIb

IIc wherein k, l and m independently represent 0, 1, 2, 3 or 4;

$R^4$ and $R^5$ independently represent H, Si(Me)$_3$, 1- or 2-naphthyl, a polycyclic hydrocarbyl group, CHR$^{41}$R$^{42}$ or $C_{1-4}$ alkyl (which latter group is optionally substituted by one or more halo substituents), or $C_{3-8}$ cycloalkyl, phenyl, methylenedioxyphenyl, benzodioxanyl, benzofuranyl, dihydrobenzofuranyl, benzothiazolyl, benzoxazolyl, benzimidazolyl, coumaranonyl, coumarinyl or dihydrocoumarinyl (which latter twelve groups are optionally substituted by one or more of $C_{1-4}$ alkyl (which latter group is optionally substituted by one or more halo substituents), $C_{1-4}$ alkoxy, halo, hydroxy, cyano, nitro, SO$_2$NH$_2$, C(O)OH or N(H)R$^{43}$);

$R^{41}$ and $R^{42}$ independently represent cyclohexyl or phenyl;

$R^6$ and $R^7$ independently represent H, $C_{1-4}$ alkyl, $C_{3-8}$ cycloalkyl, phenyl (which latter group is optionally substituted by one or more of $C_{1-4}$ alkyl (which latter group is optionally substituted by one or more halo substituents), $C_{1-4}$ alkoxy, halo, hydroxy, cyano, nitro, SO$_2$NH$_2$, C(O)OH or N(H)R$^{44}$) or together with the carbon atom to which they are attached form a $C_{3-8}$ cycloalkyl ring;

$R^{43}$ and $R^{44}$ independently represent H or C(O)R$^{45}$; and $R^{45}$ represents H, $C_{1-4}$ alkyl or $C_{1-4}$ alkoxy;

Y represents CH$_2$, (CH$_2$)$_2$, CH=CH, (CH$_2$)$_3$, CH$_2$CH=CH or CH=CHCH$_2$, which latter three groups are optionally substituted by $C_{1-4}$ alkyl, methylene, oxo or hydroxy;

n represents 0, 1, 2, 3 or 4; and

B represents a structural fragment of formula IVa, IVb, IVc or IVd,

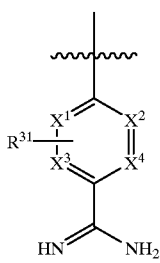
IVa

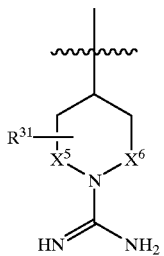
IVb

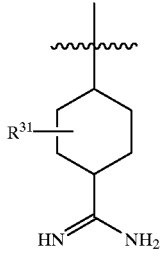
IVc

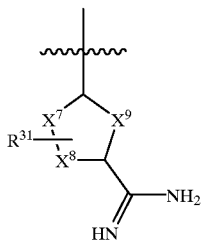
IVd wherein $X^1$, $X^2$, $X^3$ and $X^4$ independently represent CH, N or N—O;

$X^5$ and $X^6$ independently represent a single bond or CH$_2$;

one of $X^7$, $X^8$ and $X^9$ represents S, O or NH, and the other two independently represent —CH=, =CH—, —N=, =N—, —N(O)= or =N(O)—;

$R^{31}$ represents, in all cases, one or more optional substituents selected from halo, $C_{1-4}$ alkyl, $C_{1-4}$ alkoxy or —O—(CH$_2$)$_p$—C(O)N(R$^{32}$)(R$^{33}$);

p represent 0, 1, 2, 3 or 4; and $R^{32}$ and $R^{33}$ independently represent H, $C_{1-6}$ alkyl or $C_{3-7}$ cycloalkyl;

or a pharmaceutically acceptable salt thereof.

The compounds of formula I may exhibit tautomerism. All tautomeric forms and mixtures thereof are included within the scope of the invention.

The compounds of formula I may also contain one or more asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

Alkyl groups which $R^1$, $R^2$, $R^3$, $R^4$, $R^5$, $R^6$, $R^7$, $R^{11}$, $R^{12}$, $R^{13}$, $R^{14}$, $R^{15}$, $R^{16}$, $R^{17}$, $R^{18}$, $R^{19}$, $R^{31}$, $R^{32}$, $R^{33}$ and $R^{45}$ may represent, and with which $R^4$, $R^5$, $R^6$, $R^7$ and Y may be substituted; alkoxy groups which $R^{31}$ and $R^{45}$ may represent and with which $R^4$, $R^5$, $R^6$ and $R^7$ may be substituted; cycloalkyl groups which $R^2$, $R^3$, $R^4$, $R^5$, $R^6$, $R^7$, $R^{32}$, $R^{33}$, $R^{41}$ and $R^{42}$ may represent; and alkylphenyl groups which $R^{15}$ and $R^{17}$ may represent may be linear or branched, and may be saturated or unsaturated. Alkylene groups represented by $-(CH_2)_k-$, $-(CH_2)_l-$, $-(CH_2)_m-$, $-(CH_2)_n-$, $-(CH_2)_p-$ and $-(CH_2)_q-$ in compounds of formula I may be linear or branched, and may be saturated or unsaturated.

Halo groups which $R^{31}$ may represent, with which $R^4$, $R^5$, $R^6$ and $R^7$ may be substituted, and with which the substituents on $R^4$, $R^5$, $R^6$ and $R^7$ may be substituted, include fluoro, chloro, bromo and iodo.

In the structural fragments of formulae IIa, IIb and IIc, the dots indicate the carbon atom which is bonded to the $-C(O)-$ group and to the carbon atom bearing $-OR^1$, $R^2$ and $R^3$ in a compound of formula I (for the avoidance of doubt, there is no further H atom bonded to the carbon atom so indicated).

The wavy line on the bond in the fragments IVa, IVb, IVc and IVd signifies the bond position of the fragments. For the avoidance of doubt, when one or more substituent $R^{31}$ is/are present, it/they replace(s) one or more H atoms of CH, $CH_2$ and/or NH groups in the appropriate rings.

The skilled person will appreciate that, in the structural fragment IVd, two double bonds must be present in the five-membered ring, the position of which double bonds will depend upon which of $X^7$, $X^8$ and $X^9$ represents S, O or NH.

Abbreviations are listed at the end of this specification.

Preferred compounds of the invention include those in which, when B represents a structural fragment for formula IVa (in which $X^1$, $X^2$, $X^3$ and $X^4$ all represent CH), a structural fragment of formula or IVb or a structural fragment of formula or IVc, $R^{31}$ represents one or more substituents selected from halo, $C_{1-4}$ alkyl, $C_{1-4}$ alkoxy or $-O-(CH_2)_p-C(O)N(R^{32})(R^{33})$ (i.e. the substituent(s) is/are not optional).

Preferred compounds of the invention include those in which B represents a structural fragment for formula IVa.

Compounds of formula I in which the fragment

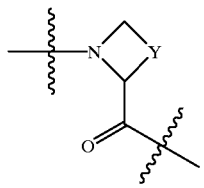

is in the S-configuration are preferred. The wavy lines on the nitrogen and carbon atom in the above fragment signify the bond position of the fragment.

Preferred compounds of formula I include the compounds of Examples 1 and 2.

Preparation

According to the invention there is also provided a process for the preparation of compounds of formula I which comprises:

(a) the coupling of a compound of formula V,

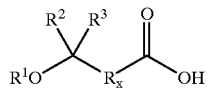

V wherein $R^1$, $R^2$, $R^3$ and $R_x$ are as hereinbefore defined with a compound of formula VI,

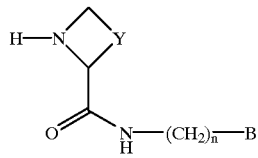

VI wherein Y, n and B are as hereinbefore defined, for example in the presence of a coupling system (e.g. oxalyl chloride in DMF, EDC, DCC, HBTU or TBTU), an appropriate base (e.g. pyridine, DMAP, TEA or DIPEA) and a suitable organic solvent (e.g. dichloromethane, acetonitrile or DMF);

(b) the coupling of a compound of formula VII,

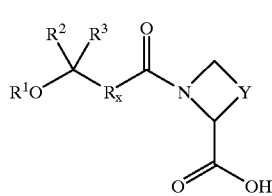

VII wherein $R^1$, $R^2$, $R^3$, $R_x$ and Y are as hereinbefore defined with a compound of formula VIII,

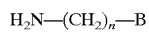

VIII wherein n and B are as hereinbefore defined, for example in the presence of a coupling system (e.g. oxalyl chloride in DMF, EDC, DCC, HBTU or TBTU), an appropriate base (e.g. pyridine, DMAP, TEA or DIPEA) and a suitable organic solvent (e.g. dichloromethane, acetonitrile or DMF);

(c) for compounds of formula I in which B represents a structural fragment of formula IVa, IVb or IVc, reaction of a compound of formula IX,

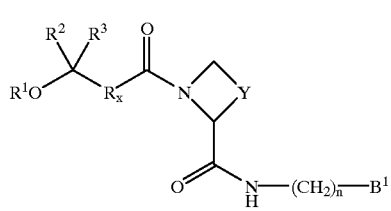

IX wherein $B^1$ represents a structural fragment of formula $IVa^1$, $IVb^1$ or $IVc^1$

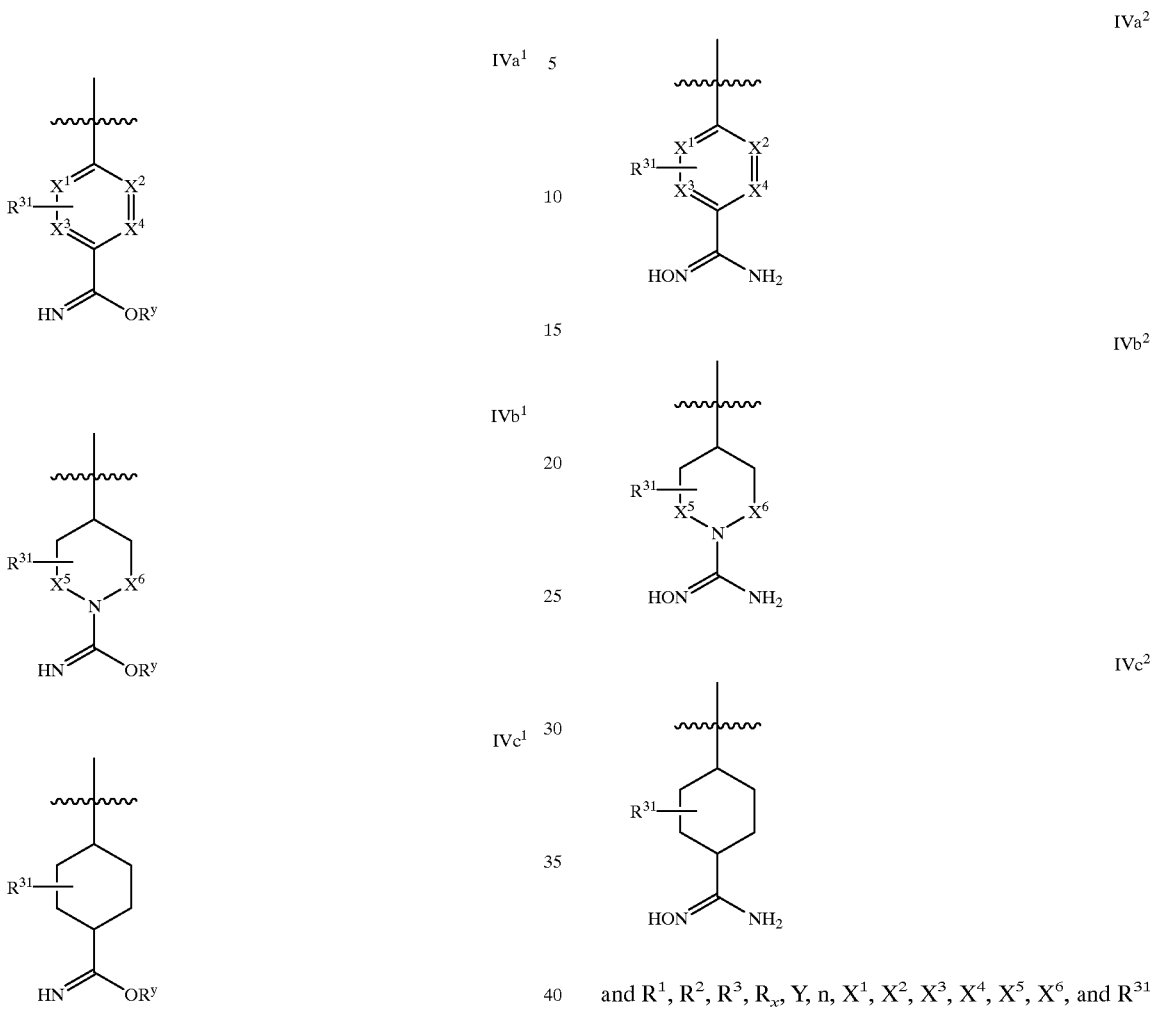

wherein $R^y$ represents $C_{1-4}$ alkyl and $R^1$, $R^2$, $R^3$, $R_x$, Y, n, $X^1$, $X^2$, $X^3$, $X^4$, $X^5$, $X^6$ and $R^{31}$ are as hereinbefore defined, with ammonia gas, for example at room temperature in the presence of a suitable organic solvent (e.g. methanol or ethanol);

(d) for compounds of formula I in which B represents a structural fragment of formula IVa, IVb or IVc, reduction of a compound of formula X,

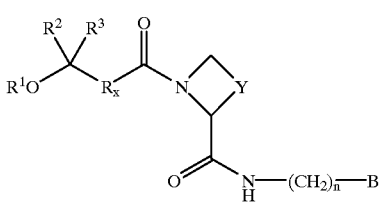

X wherein $B^2$ represents a structural fragment of formula $IVa^2$, $IVb^2$ or $IVc^2$ and $R^1$, $R^2$, $R^3$, $R_x$, Y, n, $X^1$, $X^2$, $X^3$, $X^4$, $X^5$, $X^6$, and $R^{31}$ are as hereinbefore defined, in the presence of a suitable reducing agent (for example by catalytic hydrogenation in the presence of e.g. Pd/C or $TiCi_3$) and an appropriate organic solvent (e.g. ethanol); or (e) for compounds of formula I wherein $X^1$, $X^2$, $X^3$, $X^4$, $X^7$, $X^8$ and/or $X^9$ represent N—O, oxidation of a corresponding compound of formula I in which $X^1$, $X^2$, $X^3$, $X^4$, $X^7$, $X^8$ and/or $X^9$ (as appropriate) represent N, for example under conditions which are well known to those skilled in the art.

Compounds of formula I in which B represents a structural fragment of formula IVd may be prepared analogously to methods described herein or, alternatively, analogously to the methods described in international patent applications WO 95/23609 and WO 98/06741.

Compounds of formula V are commercially available, are well known in the literature, or are available using known techniques. For example, compounds of formula V may be prepared by hydrolysis of a compound of formula XI,

XI

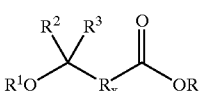

wherein R is $C_{1-6}$ alkyl or $C_{1-3}$ alkylphenyl and $R^1$, $R^2$, $R^3$ and $R_x$ are as hereinbefore defined, for example at room temperature in the presence of a suitable base (e.g. lithium hydroxide) and an appropriate solvent (e.g. THF and/or water).

Compounds of formula VI may be prepared by reaction of a compound of formula XII,

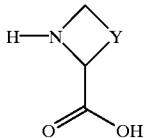

XII wherein Y is as hereinbefore defined with a compound of formula VIII as hereinbefore defined, for example under conditions such as those described hereinbefore for synthesis of compounds of formula I (process steps (a) and (b)).

Compounds of formula VII are readily available using known techniques.

For example, compounds of formula VII may be prepared by reaction of a compound of formula V as hereinbefore defined with a compound of formula XII as hereinbefore defined, for example under conditions such as those described hereinbefore for synthesis of compounds of formula I (process steps (a) and (b)).

Compounds of formula IX may be prepared by known techniques. For example, compounds of formula IX in which $B^1$ represents a structural fragment of formula $IVa^1$ or $IVc^1$ may be prepared by reaction of a compound of formula XIII,

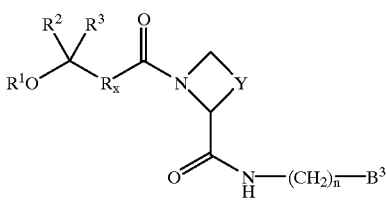

XIII wherein $B^3$ represents a structural fragment of formula $IVa^3$ or $IVc^3$,

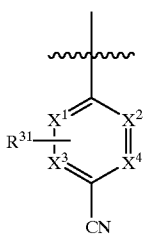

$IVa^3$

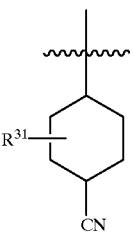

$IVc^3$ and $R^1$, $R^2$, $R^3$, $R_x$, Y, n, $X^1$, $X^2$, $X^3$, $X^4$ and $R^{31}$ are as hereinbefore defined, with HCl(g) and a $C_{1-4}$ alkyl alcohol, for example at or below room temperature.

Compounds of formula X may be prepared by known techniques. For example, compounds of formula X in which $B^2$ represents a structural fragment of formula $IVa^2$ or $IVc^2$ may be prepared by reaction of a compound of formula XIII as hereinbefore defined with HCl(g) and methanol, for example at or below room temperature, followed by reaction with hydroxylamine, or a hydrohalide salt thereof, for example at or around room temperature in the presence of an appropriate base (e.g. TEA) and a suitable solvent (e.g. MeOH).

Compounds of formula XI in which $R^1$ and $R^3$ both represent H may be prepared by reduction of a compound of formula XIV,

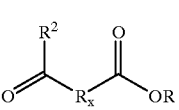

XIV wherein R, $R_x$ and $R^2$ are as hereinbefore defined, for example at below room temperature (e.g. between −70° C. and −5° C.) in the presence of a suitable reducing agent (e.g. sodium borohydride) and an appropriate organic solvent (e.g. MeOH or EtOH).

Compounds of formula XI in which $R^1$ represents H and $R^3$ represents $C_{1-4}$ alkyl, cyclohexyl or phenyl may be prepared by reaction of a compound of formula XIV as hereinbefore defined with an organometallic reagent of formula XV $R^{3a}M$  XV wherein $R^{3a}$ represents $C_{1-4}$ alkyl, cyclohexyl or phenyl, M represents Li or MgHal and Hal is Cl, Br or I, under conditions which are well known to those skilled in the art in the presence of an appropriate organic solvent (e.g. THF).

Compounds of formula XI in which $R^1$ represents H may also be prepared by reaction of a compound of formula XVI, RO—C(O)—$R_x$H   XVI wherein R and $R_x$ are as hereinbefore defined with a compound of formula XVII, $R^2$—C(O)—$R^3$   XVII wherein $R^2$ and $R^3$ are as hereinbefore defined under conditions which are well known to those skilled in the art.

Compounds of formula XI in which $R^1$, $R^2$ and $R^3$ all represent H, $R_x$ represents a structural fragment of formula IIa, as hereinbefore defined, in which neither k nor l represent 0, may be prepared by reduction of a compound of formula XVIII,

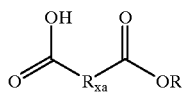

XVIII wherein $R_{xa}$ represents a structural fragment of formula IIa, as hereinbefore defined, in which neither k nor l represent 0, and R is as hereinbefore defined, in the presence of a suitable reducing agent (e.g. borane) in the presence of an appropriate organic solvent (e.g. THF).

Compounds of formula XIII may be prepared by coupling a compound of formula VII as hereinbefore defined to a compound of formula XIX,

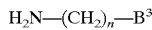

XIX wherein n and $B^3$ are as hereinbefore defined, for example under conditions such as those described hereinbefore for synthesis of compounds of formula I (process steps (a) and (b)).

Compounds of formula XIV are either known from, or may be prepared analogously to, the methods described in J. Org. Chem., 54, 3831 (1989).

Compounds of formula XVIII are well known in the literature or may be prepared using known techniques, for example by reaction of a suitable malonic acid derivative with an alkylating agent of formula XX,

XX in which L is a leaving group (e.g. halo (Cl, Br, I) or tosyl) and $R_{xa}$ is as hereinbefore defined, for example in the presence of a suitable base (e.g. sodium hydride or sodium ethoxide) and an appropriate organic solvent.

Compounds of formula VIII, XII, XV, XVI, XVII, XIX and XX and derivatives thereof, are either commercially available, are known in the literature, or may be obtained either by analogy with the processes described herein, or by conventional synthetic procedures, in accordance with standard techniques, from readily available starting materials using appropriate reagents and reaction conditions.

Substituents on inter alia phenyl groups contained in compounds of formulae I, V, VI, VII, VIII, IX, X, XI, XIII, XIV, XVI, XVIII, XIX and XX may be inter-converted using standard techniques.

Compounds of formula I may be isolated from their reaction mixtures using conventional techniques.

It will be appreciated by those skilled in the art that in the process described above the functional groups of intermediate compounds may need to be protected by protecting groups.

Functional groups which it is desirable to protect include hydroxy, amino and carboxylic acid. Suitable protecting groups for hydroxy include trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acid include $C_{1-6}$ alkyl or benzyl esters. Suitable protecting groups for amino, amidino and guanidino include t-butyloxycarbonyl or benzyloxycarbonyl. Amidino and guanidino nitrogens may be either mono- or diprotected.

The protection and deprotection of functional groups may take place before or after coupling.

For example, the compounds of formula I may be prepared by processes comprising the coupling of an N-acylated amino acid or a N-protected amino acid. When a N-protected amino acid is used the acyl group may be added after coupling and deprotection of the nitrogen atom may then be effected using standard methods thereafter.

Protecting groups may be removed in accordance with techniques which are well known to those skilled in the art and as described hereinafter.

The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Certain protected derivatives of compounds of formula I, which may be made prior to a final deprotection stage to form compounds of formula I, are novel.

According to a further aspect of the invention there is provided a compound of formula Ia,

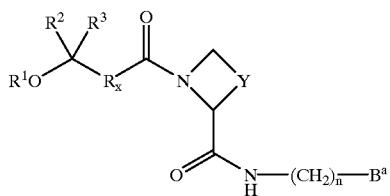

Ia wherein $B^a$ represents a structural fragment of formula IVe, IVf, IVg or IVh

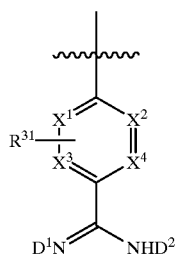

IVe

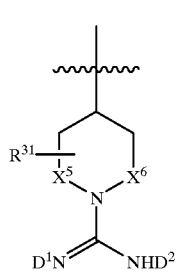

IVf

IVg

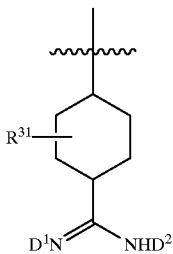

IVh

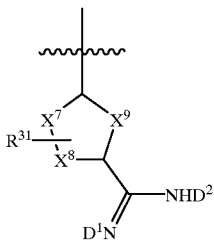

wherein $D^1$ and $D^2$ independently represent, in each case, H, OH, $OR^a$, $OC(O)R^b$, $OC(O)OR^c$, $C(O)OR^d$, $C(O)R^e$, and $R^a$, $R^b$, $R^c$, $R^d$ and $R^e$ independently represent $C_{1-12}$ alkyl (which latter group is optionally interrupted by oxygen and/or substituted by halo), phenyl, naphthyl, $C_{1-3}$ alkylphenyl (which latter three groups are optionally substituted by $C_{1-4}$ alkyl, $C_{1-4}$ alkoxy, nitro, or halo) or $-(C(R^f)(R^g))_2 OC(O)C(R^h)$, $R^f$, $R^g$ and $R^h$ independently represent H or $C_{1-4}$ alkyl, and $R^1$, $R^2$, $R^3$, $R_x$, Y, n, $X^1$, $X^2$, $X^3$, $X^4$, $X^5$, $X^6$, $X^7$, $X^8$, $X^9$ and $R^-$ are as hereinbefore defined, or a pharmaceutically acceptable salt thereof, provided that $D^1$ and $D^2$ do not both represent H.

Alkyl groups which $R^a$, $R^b$, $R^c$, $R^d$, $R^e$, $R^f$, $R^g$ and $R^h$ may represent, and with which $R^a$, $R^b$, $R^c$, $R^d$ and $R^e$ may be substituted, may be linear or branched, may be saturated or unsaturated, and may be cyclic, acyclic or part cyclic/acyclic. Alkoxy groups with which $R^a$, $R^b$, $R^c$, $R^d$ and $R^e$ may be substituted, may be linear or branched, may be saturated or unsaturated, and may be cyclic, acyclic or part cyclic/acyclic. The alkyl part of alkylphenyl groups which $R^a$, $R^b$, $R^c$, $R^d$ and $R^e$ may represent, may be linear or branched, and may be saturated or unsaturated.

Halo groups with which $R^a$, $R^b$, $R^c$, $R^d$ and $R^e$ may be substituted include fluoro, chloro, bromo and iodo.

The wavy line on the bond in the fragments IVe, IVf, IVg and IVh signifies the bond position of the fragments.

Preferred compounds of formula Ia include those wherein $D^2$ represents H and $D^1$ represents OH, $OCH_3$, $OC(O)R^b$ or $C(O)OR^d$, wherein $R^b$ and $R^d$ are as hereinbefore defined.

Structural preferences mentioned hereinbefore for compounds of formula I also apply to compounds of formula Ia.

Compounds of formula Ia may also be prepared directly from compounds of formula I in accordance with techniques well known to those skilled in the art. For example compounds of formula Ia in which $B^a$ represents a structural fragment of formula IVe, IVf or IVg, and in which $D^1$ or $D^2$ represent OH, may be prepared as described hereinbefore for compounds of formula X, or by analogous methods.

Alternatively, compounds of formula Ia in which $B^a$ represents a structural fragment of formula IVe, IVf or IVg, and in which $D^1$ or $D^2$ represent OH or $OR^a$, wherein $R^a$ is as hereinbefore defined, may be prepared from compounds of formula XIII as defined hereinbefore by reaction with a compound of formula XXI, $$H_2NOR^{a1} \qquad \text{XXI}$$

wherein $R^{a1}$ represents H or $R^a$ and $R^a$ is as hereinbefore defined, for example at between 40 and 60° C., in the presence of a suitable base (e.g. TEA) and an appropriate organic solvent (e.g. THF, $CH_3CN$, DMF or DMSO).

Compounds of formula Ia may alternatively be prepared via other protected derivatives of formula Ia in accordance with techniques well known to those skilled in the art. For example compounds of formula Ia in which $D^1$ or $D^2$ represents $OC(O)OR^c$, and $R^c$ is as hereinbefore defined, may be prepared by reaction of a corresponding compound of formula Ia in which $D^1$ or $D^2$ (as appropriate) represents OH with a compound of formula XXII, $$R^cC(O)-O-C(O)R^c \qquad \text{XXII}$$

wherein $R^c$ is as hereinbefore defined, for example at room temperature in the presence of a suitable base (e.g. TEA, pyridine or DMAP) and an appropriate organic solvent. Moreover, compounds of formula Ia in which $D^1$ or $D^2$ represents OH may be prepared by reaction of a corresponding compound of formula Ia in which $D^1$ or $D^2$ (as appropriate) represents $COOR^d$ and $R^d$ is as hereinbefore defined with hydroxylamine (or a hydrohalide salt thereof), for example at 40° C. in the presence of a suitable base (e.g. TEA) and an appropriate organic solvent (e.g. THF).

Compounds of formulae XXI and XXII are commercially available, are well known in the literature, or are available using known techniques.

It will also be appreciated by those skilled in the art that, although such protected derivatives of compounds of formula I (e.g. compounds of formula Ia) may not possess pharmacological activity as such, they may be administered parenterally or orally and thereafter metabolised in the body to form compounds of the invention which are pharmacologically active. Such derivatives may therefore be described as "prodrugs". All prodrugs of compounds of formula I are included within the scope of the invention.

Protected derivatives of compounds of formula I which are particularly useful as prodrugs include compounds of formula Ia.

Moreover, certain compounds of formula I may act as prodrugs of other compounds of formula I.

Compounds of formula I, pharmaceutically-acceptable salts, tautomers and stereoisomers thereof, as well as prodrugs thereof (including compounds of formula Ia which are prodrugs of compounds of formula I), are hereinafter referred to together as "the compounds of the invention".

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Medical and Pharmaceutical Use

The compounds of the invention are useful because they possess pharmacological activity. They are therefore indicated as pharmaceuticals.

According to a further aspect of the invention there is thus provided the compounds of the invention for use as pharmaceuticals.

In particular, the compounds of the invention are potent inhibitors of trypsin-like proteases, especially thrombin, either as such or, in the case of prodrugs, after administration to mammals including man, for example as demonstrated in the tests described below.

The compounds of the invention are thus expected to be useful in those conditions where inhibition of thrombin is required.

The compounds of the invention are thus indicated in the treatment or prophylaxis of thrombosis and hypercoagulability in blood and tissues of animals including man.

It is known that hypercoagulability may lead to thromboembolic diseases. Conditions associated with hypercoagulability and thrombo-embolic diseases which may be mentioned include activated protein C resistance, such as the factor V-mutation (factor V Leiden), and inherited or acquired deficiencies in antithrombin III, protein C, protein S, heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis. The compounds of the invention are thus indicated both in the therapeutic and/or prophylactic treatment of these conditions.

The compounds of the invention are further indicated in the treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis and pulmonary embolism, arterial thrombosis (e.g. in myocardial infarction, unstable angina, thrombosis-based stroke and peripheral arterial thrombosis) and systemic embolism usually originating from the atrium during arterial fibrillation or from the left ventricle after transmural myocardial infarction.

Moreover, the compounds of the invention are expected to have utility in prophylaxis of re-occlusion (i.e. thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis.

In addition to its effects on the coagulation process, thrombin is known to activate a large number of cells (such as neutrophils, fibroblasts, endothelial cells and smooth muscle cells). Therefore, the compounds of the invention may also be useful for the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease, cerebral arterial disease, peripheral arterial disease, reperfusion damage, and restenosis after percutaneous trans-luminal angioplasty (PTA).

Compounds of the invention that inhibit trypsin and/or thrombin may also be useful in the treatment of pancreatitis.

According to a further aspect of the present invention, there is provided a method of treatment of a condition where inhibition of thrombin is required or desired, which method comprises administration of a therapeutically effective amount of a compound of the invention, or a pharmaceutically acceptable salt thereof, to a person suffering from, or susceptible to such a condition.

The compounds of the invention will normally be administered orally, intravenously, subcutaneously, buccally, rectally, dermally, nasally, tracheally, bronchially, by any other parenteral route or via inhalation, in the form of pharmaceutical preparations comprising active compound either as a free base, or a pharmaceutical acceptable non-toxic organic or inorganic acid addition salt, in a pharmaceutically acceptable dosage form. Depending upon the disorder and patient to be treated and the route of administration, the compositions may be administered at varying doses.

The compounds of the invention may also be combined and/or co-administered with any antithrombotic agent with a different mechanism of action, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors and ADP-receptor ($P_2T$) antagonists.

The compounds of the invention may further be combined and/or co-administered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

According to a further aspect of the invention there is thus provided a pharmaceutical formulation including a compound of the invention, in admixture with a pharmaceutically acceptable adjuvant, diluent or carrier.

Suitable daily doses of the compounds of the invention in therapeutic treatment of humans are about 0.001–100 mg/kg body weight at peroral administration and 0.001–50 mg/kg body weight at parenteral administration.

The compounds of the invention have the advantage that they may be more efficacious, be less toxic, be longer acting, have a broader range of activity, be more potent, produce fewer side effects, be more easily absorbed than, or that they may have other useful pharmacological properties over, compounds known in the prior art.

Biological Tests

Test A

Determination of Thrombin Clotting Time (TT)

Human thrombin (T 6769, Sigma Chem. Co.) in buffer solution, pH 7.4, 100 μL, and inhibitor solution, 100 μL, were incubated for one min. Pooled normal citrated human plasma, 100 μL, was then added and the clotting time measured in an automatic device (KC 10, Amelumg).

The clotting time in seconds was plotted against the inhibitor concentration, and the $IC_{50}TT$ was determined by interpolation.

$IC_{50}TT$ is the concentration of inhibitor in the test that doubles the thrombin clotting time for human plasma.

Test B

Determinaton of Thrombin Inhibition with a Chromogenic, Robotic Assay

The thrombin inhibitor potency was measured with a chromogenic substrate method, in a Plato 3300 robotic microplate processor (Rosys AG, CH-8634 Hombrechtikon, Switzerland), using 96-well, half volume microtitre plates (Costar, Cambridge, Mass., USA; Cat. No. 3690). Stock solutions of test substance in DMSO (72 μL; 1 mmol/L) were diluted serially 1:3 (24+48 μL) with DMSO to obtain ten different concentrations, which were analysed as samples in the assay. 2 μL of test sample was diluted with 124 μL assay buffer, 12 μL of chromogenic substrate solution (S-2366, Chromogenix, Mölndal, Sweden) in assay buffer and finally 12 μL of α-thrombin solution, (Human α-thrombin, Sigma Chem. Co.) both in assay buffer, were added, and the samples mixed. The final assay concentrations were: test substance 0.00068–13.3 μmol/L, S-2366 0.30 mmol/L, α-thrombin 0.020 NIHU/mL. The linear absorbance increment during 40 minutes incubation at 37° C. was used for calculation of percentage inhibition for the test samples, as compared to blanks without inhibitor. The $IC_{50}$-robotic value, corresponding to the inhibitor concentration which caused 50% inhibition of the thrombin activity, was calculated from a log dose vs. % inhibition curve.

Test C

Determinaton of the Inhibition Constant $K_i$ for Human Thrombin $K_i$-determinations were made using a chromogenic substrate method, performed at 37° C. on a Cobas Bio centrifugal analyser (Roche, Basel, Switzerland). Residual enzyme activity after incubation of human α-thrombin with various concentrations of test compound was determined at three different substrate concentrations, and was measured as the change in optical absorbance at 405 nm.

Test compound solutions (100 μL; normally in buffer or saline containing BSA 10 g/L) were mixed with 200 μL of human α-thrombin (Sigma Chem. Co.) in assay buffer (0.05 mol/L Tris-HCl pH 7.4, ionic strength 0.15 adjusted with NaCl) containing BSA (10 g/L), and analysed as samples in the Cobas Bio. A 60 μL sample, together with 20 μL of water, was added to 320 μL of the substrate S-2238 (Chromogenix AB, Mölndal, Sweden) in assay buffer, and the absorbance change (ΔA/min) was monitored. The final concentrations of S-2238 were 16, 24 and 50 μmol/L and of thrombin 0.125 NIH U/mL.

The steady state reaction rate was used to construct Dixon plots, i.e. diagrams of inhibitor concentration vs. 1/(ΔA/min). For reversible, competitive inhibitors, the data points for the different substrate concentrations typically form straight lines which intercept at $x=-K_i$.

Test D

Determination of Activated Partial Thromboplastin Time (APTT)

APTT was determined in pooled normal human citrated plasma with the reagent PTT Automated 5 manufactured by Stago. The inhibitors were added to the plasma (10 μL inhibitor solution to 90 μL plasma) followed by the reagent and calcium chloride solution and APTT was determined in the mixture by use of the coagulation analyser KC10 (Amelumg) according to the instructions of the reagent producer. The clotting time in seconds was plotted against the inhibitor concentration in plasma and the $IC_{50}$APTT was determined by interpolation.

$IC_{50}$APTT is defined as the concentration of inhibitor in human plasma that doubles the Activated Partial Thromboplastin Time.

Test E

Determination of Thrombin Time ex vivo

The inhibition of thrombin after oral or parenteral administration of the compounds of the formula I and Ia, dissolved in ethanol:Solutol™:water (5:5:90), were examined in conscious rats which, one or two days prior to the experiment, were equipped with a catheter for blood sampling from the carotid artery. On the experimental day blood samples were withdrawn at fixed times after the administration of the compound into plastic tubes containing 1 part sodium citrate solution (0.13 mol per L.) and 9 parts blood. The tubes were centrifuged to obtain platelet poor plasma. The plasma was used for determination of thrombin time as described below.

The citrated rat plasma, 25 μL, was diluted with a saline solution, 0.9%, 25 μL, and plasma coagulation was started by the addition of human thrombin (T 6769, Sigma Chem. Co., USA) in a buffer solution, pH 7.4, 25 μL. The clotting time was measured in an automatic device (KC 10A-micron, Amelumg, Germany).

Where a compound of formula Ia was administered, concentrations of the appropriate active thrombin inhibitor of formula I in the rat plasma were estimated by the use of standard curves relating the thrombin time in the pooled citrated rat plasma to known concentrations of the corresponding "active" thrombin inhibitor dissolved in saline.

Based on the estimated plasma concentrations of the active thrombin inhibitor of formula I (which assumes that thrombin time prolongation is caused by the aforementioned compound) in the rat, the area under the plasma concentration-time curve after oral and/or parenteral administration of the corresponding compound of formula Ia was calculated (AUCpd) using the trapezoidal rule and extrapolation of data to infinity.

The bioavailability of the active thrombin inhibitor of formula I after oral or parenteral administration of the compound of formula Ia was calculated as below:

[(AUCpd/dose)/(AUCactive,parenteral/dose)]×100 where AUCactive,parenteral represents the AUC obtained after parenteral administration of the corresponding active thrombin inhibitor of formula I to conscious rats as described above.

Test F

Determination of Thrombin Time in Urine ex vivo

The amount of the active thrombin inhibitor of formula I that was excreted in urine after oral or parenteral administration of the compounds of the invention, dissolved in ethanol:Solutol™:water (5:5:90), was estimated by determination of the thrombin time in urine ex vivo (assuming that thrombin time prolongation is caused by the aforementioned compound).

Conscious rats were placed in metabolism cages, allowing separate collection of urine and faeces, for 24 hours following oral administration of compounds of the invention. The thrombin time was determined on the collected urine as described below.

Pooled normal citrated human plasma (100 μL) was incubated with the concentrated rat urine, or saline dilutions thereof, for one minute. Plasma coagulation was then initiated by the administration of human thrombin (T 6769, Sigma Chem. Co.) in buffer solution (pH 7.4; 100 μL). The clotting time was measured in an automatic device (KC 10; Amelumg).

The concentrations of the active thrombin inhibitor of formula I in the rat urine were estimated by the use of standard curves relating the thrombin time in the pooled normal citrated human plasma to known concentrations of the aforementioned active thrombin inhibitor dissolved in concentrated rat urine (or saline dilutions thereof). By multiplying the total rat urine production over the 24 hour period with the estimated mean concentration of the aforementioned active inhibitor in the urine, the amount of the active inhibitor excreted in the urine (AMOUNTpd) could be calculated.

The bioavailability of the active thrombin inhibitor of formula I after oral or parenteral administration of the prodrug was calculated as below:

[(AMOUNTpd/dose)/(AMOUNTactive,parenteral/dose)]×100 where AMOUNTactive,parenteral represents the amount excreted in the urine after parenteral administration of the corresponding active thrombin inhibitor of formula I to conscious rats as described above.

The invention is illustrated by way of the following examples.

EXAMPLES

General Experimental Procedures

Mass spectra were recorded on a Finnigan MAT TSQ 700 triple quadrupole mass spectrometer equipped with an electrospray interface (FAB-MS) and VG Platform II mass spectrometer equipped with an electrospray interface (LC-MS). $^1$H NMR and $^{13}$C NMR measurements were performed on BRUKER ACP 300 and Varian UNITY plus 400, 500 and 600 spectrometers, operating at $^1$H frequencies of 300.13, 399.96, 499.82 and 599.94 MHz respectively, and at $^{13}$C frequencies of 75.46, 100.58, 125.69 and 150.88 MHz respectively. Preparative HPLC was performed on reverse phase columns (250 mm, 20 or 50 mm; 5 to 7 μM phase Chromasil C8) with flow rates of 10 to 50 mL/min using a UV detector (240 to 290 nm).

Example 1

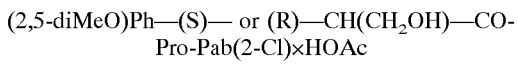
(2,5-diMeO)Ph—(S)— or (R)—CH(CH$_2$OH)—CO-Pro-Pab(2-Cl)×HOAc

(i) 4-Azidomethyl-3-chlorobenzonitrile

A mixture 8.0 g (0.035 mol) of 4-bromomethyl-3-chlorobenzonitrile (J. Pharm. Sci., (1986) 75, 410), 2.7 g (0.042 mol) of sodium azide, 1.2 g (3.4 mmol) of tetrabutylammonium hydrogen sulfate, 0.30 g (3.4 mmol) of sodium hydrogen carbonate, 7 mL of water and 20 mL of toluene was stirred vigorously for 3 days. The phases were separated and the aqueous layer was extracted three times with ether. The combined organic phase was washed with water, dried over sodium sulfate and evaporated to give 6.7 g (100%) of the sub-title compound.

$^1$H-NMR (300 MHz; CDCl$_3$): δ4.60 (s, 2H), 7.57 (d, 1H), 7.61 (m, 1 H), 7.70 (d, 1H)

(ii) 4-Aminomethyl-3-chlorobenzonitrile

4-Azidomethyl-3-chlorobenzonitrile (1.0 g; 5.2 mmol; from step (i) above), was dissolved in 9 mL of water and 1 mL of ethanol. Triphenylphosphine (1.5 g) was added, and the mixture was stirred overnight. The ethanol was evaporated and the residue was partitioned between 1M HCl and benzene. The aqueous layer was extracted several times with benzene and then freeze dried. The yield of the amine hydrochloride was 0.54 g (51%).

$^1$H-NMR (400 MHz; D$_2$O) HCl salt: δ4.42 (s, 2H), 7.69 (d, 1H), 7.81 (dd, 1 H), 7.98 (d, 1 H)

(iii) (R,S)-3-Hydroxy-2-(2,5-dimethoxyphenyl)propionic acid ethylester

To a solution of 3-oxo-2-(2,5-dimethoxyphenyl)propionic acid ethyl ester (7.6 g; 30 mmol; prepared according to the method described in J. Org. Chem. 54, 3831 (1989)) in ethanol was added NaBH$_4$ (2 equivalents) at –15° C. After stirring for 2 h at –15° C., and 4 h at –5° C., water was added, the reaction mixture was concentrated and the resultant extracted with ethyl acetate. The organic phase was washed with brine, dried (MgSO$_4$) and concentrated to give the sub-title compound. Yield 7.7 g (100%).

(iv) (2,5-diMeO)Ph-(R,S)CH(CH$_2$OH)—COOH

The ethylester from step (iii) above (7.4 g; 29 mmol) was dissolved in THF:water (1:1). LiOH×H$_2$O (2 eq.) was added and the reaction mixture was stirred for 2 h at room temperature. The reaction mixture was concentrated and extracted with CH$_2$Cl$_2$. The aqueous phase was acidified (pH 2) with HCl (2M) and extracted three times which CH$_2$Cl2. The organic phases were combined, dried (NaSO$_4$) and concentrated to give the sub-title compound. Yield 5.4 g (82%).

$^1$H-NMR (400 MHz; CDCl$_3$): δ6.89 (d, 1H); 6.85 (d, 1H); 6.78 (dd, 1H); 4.86 (broad, 2H); 4.14 (dd, 1H); 3.98 (dd, 1H); 3.78 (s, 3H); 3.72 (s, 3H); 3.67 (dd, 1H)

(v) (2,5-diMeO)Ph-(R,S)CH(CH$_2$OH)—CO-Pro-OBn 1.8 mL (9.6 mmol) of diisopropylethylamine was added to an ice-cooled mixture of 0.50 g (2.2 mmol) of (2,5-diMeO)Ph-(R,S)CH(CH$_2$OH)—COOH (from step (iv) above), 0.58 g (2.4 mmol) of H-Pro-OBn and 0.77 g (2.4 mmol) of TBTU in 10 mL of DMF. The mixture was stirred at room temperature overnight, and was then poured into 1M HCl and extracted twice with ethyl acetate:toluene (1:1). The combined organic layer was washed with NaHCO$_3$ (aq.) and water, dried (Na$_2$SO$_4$) and evaporated. The product was pure and was used directly in the next step.

Yield: 0.91 g (100%).

$^1$H-NMR (500 MHz;CDCl$_3$) diastereomeric mixture: δ1.8–2.3 (m, 4H), 3.0–3.1 (m, 1H), 3.18 (m, 1H, diastereomer), 3.34 (m, 1H, diastereomer), 3.46 (m, 1H, diastereomer), 3.65–3.7 (m, 1H), 3.75–3.9 (m, 7H, thereof 4 singlets at 3.77, 3.80, 3.85 and 3.87 ppm), 3.95–4.05 (m, 1H), 4.39 (m, 1H, diastereomer), 4.46 (m, 1H, diastereomer), 4.58 (m, 1H, diastereomer), 4.63 (m, 1H, diastereomer), 5.18 (d, 1H, diastereomer), 5.26 (s, 1H, diastereomer), 5.32 (d, 1H, diastereomer), 5.37 (s, 1H, diastereomer), 6.8–7.0 (m, 3H), 7.2–7.5 (m, 5H)

(vi) (2,5-diMeO)Ph-(R,S)CH(CH$_2$OH)—CO-Pro-OH (2,5-diMeO)Ph-(R,S)CH(CH$_2$OH)—CO-Pro-OBn (0.91 g; 2.2 mmol; from step (v) above), was hydrogenated for 2 h at atmospheric pressure over 50 mg of 10% Pd/C in 25 mL of ethanol. The mixture was filtered through celite and evaporated to give 0.71 g (100%) of the sub-title compound.

$^1$H-NMR (500 MHz; CDCl$_3$) diastereomeric mixture: δ1.8–2.3 (m, 4H), 3.02 (m, 1H, diastereomer), 3.15 (m, 1H, diastereomer), 3.47 (m, 1H, diastereomer), 3.7–3.8 (m, 5H, thereof the other diastereomer corresponding to 3.47, and two singlets at 3.74 and 3.76 ppm), 3.83–3.85 (m, 3H), 4.0–4.1 (m, 1H), 4.38 (m, 1H, diastereomer), 4.50 (m, 1H, diastereomer), 4.56 (m, 1H, diastereomer), 4.63 (m, 1H, diastereomer),6.8–6.9 (m, 3H)

(vii) (2,5-diMeO)Ph—(R and S)CH(CH$_2$OH)—CO-Pro-NHCH$_2$-Ph(2-Cl,4-CN)

0.76 mL (4.4 mmol) of diisopropylethylamine was added to an ice-cooled mixture of 0.35 g (1.1 mmol) of (2,5-diMeO)Ph-(R,S)CH(CH$_2$OH)—CO-Pro-OH (from step (vi) above), 0.22 g (1.1 mmol) of 4-aminomethyl-3-chlorobenzonitrile (from step (ii) above) and 0.35 g (1.1 mmol) of TBTU in 10 mL of DMF. The mixture was stirred at room temperature for two days, poured into 1M HCl and extracted twice with ethyl acetate:toluene (1:1). The combined organic layer was washed with NaHCO$_3$ (aq.) and water, dried (Na$_2$SO$_4$) and evaporated. The crude product was flash chromatographed on silica gel with EtOAc:MeOH (99:1) as eluant. The diastereomers separated. Total yield: 0.48 g (94%). The initial diastereomer (A) was isolated in a yield of 0.22 g.

Diastereomer A $^1$H-NMR (400 MHz; CDCl$_3$): δ1.7–2.1 (m, 3H), 2.34 (m, 1H), 2.90 (m, 1H), 3.12 (m, 1H), 3.61 (m, 1H), 3.73–3.8 (m, 4H, thereof one singlet at 3.75), 3.82 (s, 3H), 4.01 (m, 1H), 4.44 (m, 1H), 4.56 (m, 1H), 4.65 (m, 1H), 6.75–6.85 (m, 3H), 7.53 (d, 1 H), 7.56 (dd, 1 H), 7.65 (d, 1H), 7.68 (m, 1H)

(viii) (2,5-diMeO)Ph—(R or S)CH(CH$_2$OH)—CO-Pro-NHCH$_2$-Ph(2-Cl,4-C(NH)OMe)

(2,5-diMeO)Ph-(R or S)CH(CH$_2$OH)—CO-Pro-NHCH$_2$-Ph(2-Cl,4-CN) (0.22 g; 0.47 mmol; diastereomer A from step (vii) above) was dissolved in 25 mL of methanol saturated with hydrogen chloride gas and put in the refrigerator for two days. Evaporation yielded a crude material which was used in the next step without further purification.

MS (M+1)$^+$ 504

(ix) (2,5-diMeO)Ph—(R or S)CH(CH$_2$OH)—CO-Pro-Pab(2-Cl)×HOAc

Half of the crude material from step (viii) above was dissolved in 25 mL of methanol saturated with ammonia and allowed to stand at room temperature for five days. The solvent was evaporated and the residue was purified on preparative HPLC with CH$_3$CN:0.1 M NH$_4$OAc (30:70). Freeze drying from water gave 9 mg (7%) of the desired product.

$^1$H-NMR (400 MHz; D$_2$O) rotamers: δ1.8–2.4 (m, 7H, thereof one singlet at 1.93 ppm), 3.35 (m, 1H), 3.63 (m, 1H), 3.7–3.9 (m, 8H, thereof singlets at 3.80, 3.81 and 3.86 ppm (rotamers)), 4.05 (m, 1H), 4.4–4.65 (m, 3H), 6.82 (d, 1H, major rotamer), 6.86 (d, 1H, minor rotamer), 6.95–7.05 (m, 1H), 7.08 (d, 1H, major rotamer), 7.23 (d, 1H, minor rotamer), 7.59 (d, 1H), 7.63 (dd, 1H, minor rotamer), 7.73 (dd, 1H, major rotamer), 7.82 (d, 1H, minor rotamer), 7.98 (d, 1H, major rotamer) $^{13}$C-NMR (100 MHz; D$_2$O) carbonyl and amidine carbons: δ176.2, 174.6, 166.7

Example 2

(2,5-diMeO)Ph—(R or S)CH(CH$_2$OH)—CO-Pro-Pab(2-Me)×HOAc (i) 3-Methyl-4-vinylbenzonitrile 0.75 g (0.65 mmol) of tetrakis(triphenylphosphine)palladium(0) was added to a solution of 5.1 g (0.026 mol) of 4-bromo-3-methylbenzonitrile and 8.3 g (0.026 mol) of vinyltributyltin in 250 mL of toluene under argon, and the reaction was heated at reflux overnight. The mixture was filtered through a layer of celite and evaporated. The residue was flash chromatographed on silica gel with heptane:EtOAc (1:1) as eluant. Yield: 4.0 g (100%).

$^1$H-NMR (300 MHz; CDCl$_3$): δ2.36 (s, 3H), 5.46 (d, 1H), 5.73 (d, 1H), 6.90 (dd, 1H), 7.4–7.5 (m, 2H), 7.52 (d, 1H)

(ii) 4-Hydroxymethyl-3-methylbenzonitrile

3-Methyl-4-vinylbenzonitrile (0.40 g; 2.8 mmol; from step (i) above) was dissolved in 50 mL of methanol and cooled to –70° C. Ozone (2 eq.) was bubbled through, and then 0.20 g (5.3 mmol) of sodium borohydride and 5 mL of water were added and the cooling bath was removed. After 4 h the methanol was evaporated and the residue was partitioned between 1M HCl and ether. The aqueous layer was extracted twice with ether and the combined organic phase was washed with water, dried (Na$_2$SO$_4$) and evaporated to yield 0.37 g (90%) of the desired product, which was used in the next step without further purification.

$^1$H-NMR (400 MHz; CDCl$_3$): δ2.29 (s, 3H), 3.07 (broad, 1H), 4.69 (s, 2H), 7.37 (s, 1H), 7.45 (d, 1H), 7.53 (d, 1H)

(iii) 4-Methanesulfonyloxy-3-methylbenzonitrile 1.2 g (0.010 mol) of methylsulfonyl chloride was added dropwise to a solution of 1.5 g (0.010 mol) of 4-hydroxymethyl-3-methylbenzonitrile (from step (ii) above) and 1.0 g (0.010 mol) of triethylamine in 50 mL of methylene chloride at 0° C. The reaction mixture was stirred at room temperature for 3 h, washed with 1M HCl, water, dried (Na$_2$SO$_4$) and evaporated. Yield: 2.1 g (91%).

$^1$H-NMR (300 MHz; CDCl$_3$): δ2.41 (s, 3H), 3.03 (s, 3H), 5.28 (s, 2H), 7.4–7.6 (m, 3H)

(iv) 4-Azidomethyl-3-methylbenzonitrile 1.0 g (0.015 mol) of sodium azide and 10 mL of water were added to a solution of 2.1 g (9.3 mmol) of 4-methanesulfonyloxy-3-methylbenzonitrile (from step (iii) above) in 20 mL of DMF. The reaction mixture was stirred for 1.5 h at room temperature, poured into 200 mL of water and extracted three times with ether. The combined organic phase was washed several times with water, dried (Na$_2$SO$_4$) and evaporated. Yield: 1.4 g (87%).

$^1$H-NMR (300 MHz; CDCl$_3$): δ2.39 (s, 3H), 4.40 (s, 2H), 7.40 (d, 1H), 7.45–7.55 (m, 2H)

(v) 4-Aminomethyl-3-methylbenzonitrile

The sub-title compound was prepared according to the method described in Example 1(ii) above from 1.4 g (8.1 mmol) of 4-azidomethyl-3-methylbenzonitrile (from step (iv) above) and 2.3 g (9.0 mmol) of triphenylphosphine in 18 mL of ethanol and 2 mL of water. Yield: 0.60 g (contaminated by triphenylphosphine oxide; estimated actual yield: 0.36 g (28%)).

$^1$H-NMR (300 MHz; CDCl$_3$): δ2.38 (s, 3H), 3.90 (bs, 2H), 7.3–7.4 (m, 3H) obscured by triphenylphosphine oxide (vi) (2,5-diMeO)Ph—(R and S)CH(CH$_2$OH)—CO-Pro-NHCH$_2$-Ph(2-Me,4-CN)

The sub-title compound was prepared according to the method described in Example 1(vii) above from 0.37 g (1.2 mmol) of (2,5-diMeO)Ph-(R,S)CH(CH$_2$OH)—CO-Pro-OH (see Example 1(vi) above), 0.42 g of 4-aminomethyl-3-methylbenzonitrile (from step (v) above; estimated content of pure material: 0.25 g (1.7 mmol)), 0.38 g (1.2 mmol) of TBTU and 0.62 g (4.8 mmol) of diisopropylethylamine in 10 mL of DMF. The crude product was flash chromatographed on silica gel with EtOAc:acetone (9:1) as eluant. The two diastereomers separated. Total yield: 0.58 g contaminated by triphenylphosphine oxide; estimated actual yield: 0.45 g (87%). The first diastereomer to be eluted was isolated as diastereomer A.

Diastereomer A (yield: 0.30 g; contaminated by triphenylphosphine oxide; estimated actual yield: 0.20 g)

$^1$H-NMR (600 MHz; CDCl$_3$): δ1.7–2.1 (m, 3H), 2.3–2.35 (m, 4H, thereof one singlet at 2.32 ppm), 3.1–3.2 (m, 1H), 3.65 (m, 1H), 3.7–3.8 (m, 4H, thereof one singlet at 3.73 ppm), 3.80 (s, 3H), 3.98 (m, 1H), 4.4–4.5 (m, 3H), 4.65 (m, 1H), 6.7–6.9 (m, 3H), 7.37 (d, 1H), 7.41 (s, 1H), the remaining aromatic signal obscured by triphenylphosphine oxide.

(vii) (2,5-diMeO)Ph-(R or S)CH(CH$_2$OH)—CO-Pro-NHCH$_2$-Ph(2-Me,4-C(NH)OMe)

(2,5-diMeO)Ph-(R or S)CH(CH$_2$OH)—CO-Pro-NHCH$_2$-Ph(2-Me,4-CN) (0.30 g; estimated content of pure material: 0.20 g (0.44 mmol); diastereomer A from step (vi) above) was dissolved in 25 mL of methanol saturated with hydrogen chloride gas and allowed to stand at room temperature overnight. Evaporation yielded a crude material which was used without further purification. According to TLC (EtOAc:acetone; 9:1) no starting material was left.

(viii) (2,5-diMeO)Ph-(R or S)CH(CH$_2$OH)—CO-Pro-Pab(2-Me)(OH)

The crude product from step (vii) above was dissolved 10 mL of methanol and 0.14 g (2.0 mmol) of hydroxylamine hydrochloride and 0.40 g (4.0 mmol) of triethylamine were added. The mixture was allowed to stand at room temperature for two days. Evaporation and flash chromatography on silica gel with CH$_2$Cl$_2$:MeOH (9:1) gave 0.13 g (60%) of the desired compound.

¹H-NMR (600 MHz; CDCl₃): δ1.80 (m, 1H), 1.93 (m, 1H), 2.08 (m, 1H), 2.20 (s, 3H), 2.27 (m, 1H), 3.22 (m, 1H), 3.65–3.8 (m, 5H, thereof one singlet at 3.74 ppm), 3.80 (s, 3H), 4.06 (m, 1H), 4.32 (dd, 1H), 4.38 (dd, 1H), 4.51 (m, 1H), 4.71 (m, 1H), 4.93 (broad, 2H), 6.78 (dd, 1H), 6.81 (d, 1H), 6.85 (d, 1H), 7.08 (d, 1H), 7.16 (d, 1H), 7.20 (s, 1H), 7.81 (bt, 1H).

¹C—NMR (100 MHz; CDCl₃) carbonyl and amidine carbons: δ174.7, 172.8, 154.9.

(ix) (2,5-diMeO)Ph-(R or S)CH(CH₂-OH)—CO-Pro-Pab(2-Me)

(2,5-diMeO)Ph-(R or S)CH(CH₂OH)—CO-Pro-Pab(2-Me)(OH) (65 mg; 0.13 mmol; from step (viii) above) was dissolved in 5 mL of ethanol. HOAc (8 drops from a Pasteur pipette) and 40 mg of 10% Pd/C were added. The reaction mixture was hydrogenated at atmospheric pressure for two days. The reaction mixture was filtered through celite and evaporated. The residue was dissolved in water, washed with ethyl acetate and freeze dried. Yield: 46 mg (65%).

¹H-NMR (500 MHz; D₂O) rotamers: δ1.8–2.1 (m, 6H, thereof one singlet at 1.92 ppm), 2.2–2.4 (m, 4H, thereof two singlets at 2.24 (minor rotamer) and 2.38 (major rotamer)), 3.35 (m, 1H, minor rotamer), 3.6–3.7 (m, 1H), 3.75–3.85 (m, 7H, thereof three singlets at 3.77, 3.79 and 3.84 ppm (rotamers)), 4.0–4.1 (m, 1H), 4.4–4.5 (m, 3H), 4.8 (m, 1H partially obscured by the HDO peak), 6.80 (d, 1H, major rotamer), 6.85 (d, 1H, minor rotamer), 6.9–7.1 (m, 2H), 7.45 (d, 1H, major rotamer), 7.51 (d, 1H, minor rotamer), 7.55–7.65 (m, 2H)

¹³C-NMR (75 MHz; D₂O) carbonyl and amidine carbons: δ175.4, 174.5 (minor), 174.2 (minor), 174.1, 167.1.

Example 3

The title compounds of Examples 1 and 2 were tested in Test A above and were both found to exhibit an $IC_{50}TT$ value of less than 0.3 μM.

ABBREVIATIONS aq=aqueous
Bn=benzyl
DCC=dicyclohexylcarbodiimide
DIPEA=diisopropylethylamine
DMAP=N,N-dimethyl amino pyridine
DMF=dimethylformamide
DMSO=dimethylsulphoxide
EDC=1-(3-dimethylaminopropyl)-3-ethylcarbodiimide hydrochloride
Et=ethyl
EtOAc=ethyl acetate
EtOH=ethanol
h=hours
HBTU=[N,N,N',N'-tetramethyl-O-(benzotriazol-1-yl)uronium hexafluorophosphate]
HOAc=acetic acid
H-Pab=4-amidinobenzylamine
H-Pab(Z)=4-(N-benzyloxycarbonylamidino)benzylamine
H-Pab(2-Cl)=4-amidino-2-chloro-benzylamine
H-Pab(2-Me)=4-amidino-2-methyl-benzylamine
HPLC=high performance liquid chromatography
Me=methyl
MeOH=methanol
Ph=phenyl
Pr=propyl
i-PrOH=i-propanol
TBTU=[N,N,N',N'-tetramethyl-O-(benzotriazol-1-yl)uronium tetrafluoroborate]
TEA=triethylamine
THF=tetrahydrofuran
Z=benzyloxy carbonyl Prefixes n, s, i and t have their usual meanings: normal, iso, sec and tertiary. The stereochemistry for the amino acids is by default (S) if not otherwise stated.

What is claimed is:

1. A compound of formula I,

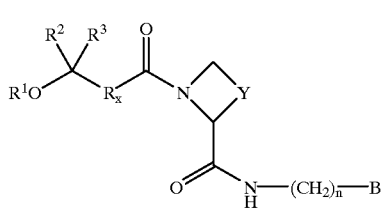

wherein
$R^1$ represents H, $C(O)R^{11}$, $SiR^{12}R^{13}R^{14}$ or $C_{1-6}$ alkyl (which latter group is optionally substituted or terminated by one or more substituents selected from $OR^{15}$ or $(CH_2)_qR^{16}$);

$R^{12}$, $R^{13}$ and $R^{14}$ independently represent H, phenyl or $C_{1-6}$ alkyl;

$R^{16}$ represents $C_{1-4}$ alkyl, phenyl, OH, $C(O)OR^{17}$ or $C(O)N(H)R^{18}$;

$R^{18}$ represents H, $C_{1-4}$ alkyl or $CH_2C(O)OR^{19}$;

$R^{15}$ and $R^{17}$ independently represent H, $C_{1-6}$ alkyl or $C_{7-9}$ alkylphenyl;

$R^{11}$ and $R^{19}$ independently represent H or $C_{1-4}$ alkyl; and q represents 0, 1 or 2;

$R^2$ and $R^3$ independently represent H, $C_{1-4}$ alkyl, cyclohexyl or phenyl;

$R_x$ represents a structural fragment of formula IIa, IIb or IIc,

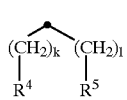

wherein
k, l and m independently represent 0, 1, 2, 3 or 4;

$R^4$ and $R^5$ independently represent H, Si(Me)₃, 1- or 2-naphthyl, a polycyclic hydrocarbyl group, $CHR^{41}R^{42}$ or $C_{1-4}$ alkyl (which latter group is optionally substituted by one or more halo substituents), or $C_{3-8}$ cycloalkyl, phenyl, methylenedioxyphenyl, benzodioxanyl, benzofuranyl, dihydrobenzofuranyl, benzothiazolyl, benzoxazolyl, benzimidazolyl, coumaranonyl, coumarinyl or dihydrocoumarinyl (which latter twelve groups are optionally substituted by one or more of $C_{1-4}$ alkyl (which latter group is optionally substituted by one or more halo substituents), $C_{1-4}$ alkoxy, halo, hydroxy, cyano, nitro, $SO_2NH_2$, C(O)OH or $N(H)R^{43}$);

$R^{41}$ and $R^{42}$ independently represent cyclohexyl or phenyl;

$R^6$ and $R^7$ independently represent H, $C_{1-4}$ alkyl, $C_{3-8}$ cycloalkyl, phenyl (which latter group is optionally substituted by one or more of $C_{1-4}$ alkyl (which latter group is optionally substituted by one or more halo substituents), $C_{1-4}$ alkoxy, halo, hydroxy, cyano, nitro, $SO_2NH_2$, C(O)OH or $N(H)R^{44}$) or together with the carbon atom to which they are attached form a $C_{3-8}$ cycloalkyl ring;

$R^{43}$ and $R^{44}$ independently represent H or $C(O)R^{43}$; and $R^{45}$ represents H, $C_{1-4}$ alkyl or $C_{1-4}$ alkoxy;

Y represents $CH_2$, $(CH_2)_2$, CH=CH, $(CH_2)_3$, $CH_2CH=CH$ or $CH=CHCH_2$, which latter three groups are optionally substituted by $C_{1-4}$ alkyl, methylene, oxo or hydroxy;

n represents 0, 1, 2, 3 or 4; and

B represents a structural fragment of formula IVa, IVb, IVc or IVd,

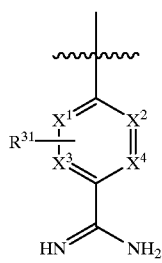

IVa

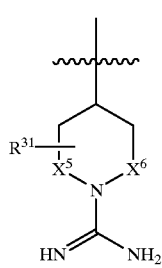

IVb

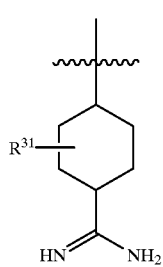

IVc

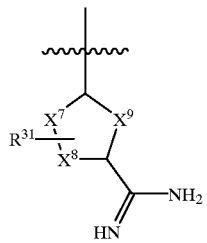

IVd wherein $X^1$, $X^2$, $X^3$ and $X^4$ independently represent CH, N or N—O;

$X^5$ and $X^6$ independently represent a single bond or $CH_2$; one of $X^7$, $X^8$ and $X^9$ represents S, O or NH, and the other two independently represent —CH=, =CH—, —N=, =N—, —N(O)= or =N(O)—;

$R^{31}$ represents, in all cases, one or more optional substituents selected from halo, $C_{1-4}$ alkyl, $C_{1-4}$ alkoxy or —O—$(CH_2)_p$—$C(O)N(R^{32})(R^{33})$;

p represents 0, 1, 2, 3 or 4; and $R^{32}$ and $R^{33}$ independently represent H, $C_{1-6}$ alkyl or $C_{3-7}$ cycloalkyl;

wherein, when B represents a structural fragment for formula IVA (in which $X^1$, $X^2$, $X^3$, and $X^4$ all represent CH), a structural fragment of formula or IVB or a structural fragment of formula or IVc, $R^{31}$ represents one or more substituents selected from halo, $C_{1-4}$ alkyl, $C_{1-4}$ alkoxy or —O-$(CH_2)_p$-C(O)N $(R^{32})(R^{33})$; or a pharmaceutically acceptable salt thereof.

or a pharmaceutically acceptable salt thereof.

2. A compound of formula I, as defined in claim 1, wherein B represents a structural fragment for formula IVa.

3. A compound of formula I, as defined in claim 1, wherein the fragment

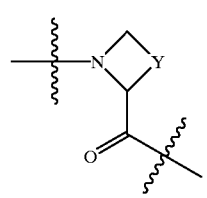

is in the S-configuration.

4. A compound of formula Ia,

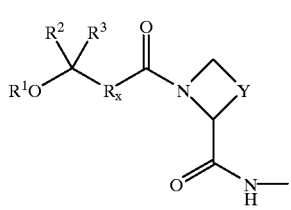

Ia wherein $B^a$ represents a structural fragment of formula IVe, IVf, IVg or IV IVe

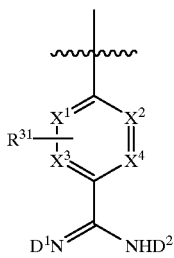

IVf

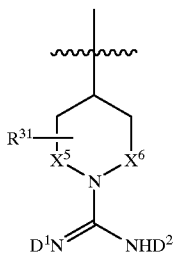

IVg

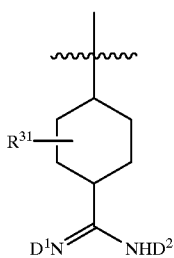

IVh

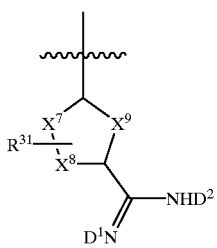

wherein $D^1$ and $D^2$ independently represent, in each case, H, OH, $OR^a$, $OC(O)R^b$, $OC(O)OR^c$, $C(O)OR^d$, $C(O)R^e$, and $R^a$, $R^b$, $R^c$, $R^d$ and $R^e$ independently represent $C_{1-12}$ alkyl (which latter group is optionally interrupted by oxygen and/or substituted by halo), phenyl, napthyl, $C_{1-3}$ alkylphenyl (which latter three groups are optionally substituted by $C_{1-4}$ alkyl $C_{1-4}$ alkoxy, nitro, or halo) or $-(C(R^f)(R^g))_2OC(O)C(R^h)$, $R^f$, $R^g$ and $R^h$ independently represent H or $C_{1-4}$ alkyl, and $R^1$, $R^2$, $R^3$, $R\_hd x$, Y, n, $X^1$, $X^2$, $X^3$, $X^4$, $X^5$, $X^6$, $X^7$, $X^8$, $X^9$ and $R^{31}$ are as defined in claim 1, or a pharmaceutically acceptable salt thereof, provided that $D^1$ and $D^2$ do not both represent H.

5. A pharmaceutical formulation including a compound as defined in claim 1, or a pharmaceutically acceptable salt thereof, in admixture with a pharmaceutically acceptable adjuvant, diluent or carrier.

6. A method of treatment of a condition where inhibition of thrombin is required or desired which method comprises administration of a therapeutically effective amount of a compound as defined in claim 1 or a pharmaceutically acceptable salt thereof, to a person suffering from, or susceptible to, such a condition.

7. A method as claimed in claim 6, wherein the condition is thrombosis.

8. A method as claimed in claim 6, wherein the condition is hypercoagulability in blood and tissues.

9. A process for the preparation of a compound of formula I which comprises:

(a) the coupling of a compound of formula V,

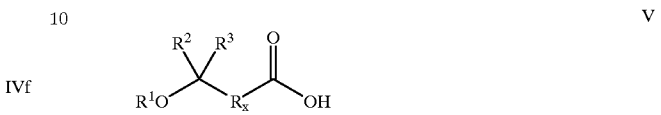

V wherein $R^1$, $R^2$, $R^3$ and $R_x$ are as defined in claim 1 with a compound of formula VI,

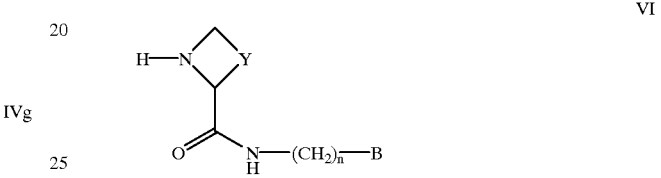

VI wherein Y, n and B are as defined in claim 1;

(b) the coupling of a compound of formula VII,

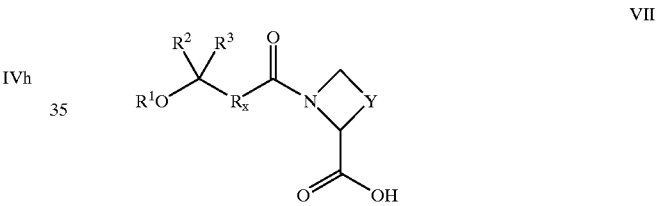

VII wherein $R^1$, $R^2$, $R^3$, $R_x$ and Y are as defined in claim 1 with a compound of formula VIII,

VIII $H_2N-(CH_2)_n-B$ wherein n and B are as defined in claim 1;

(c) for compounds of formula I in which B represents a structural fragment of formula IVa, IVb or IVc, reaction of a compound of formula IX,

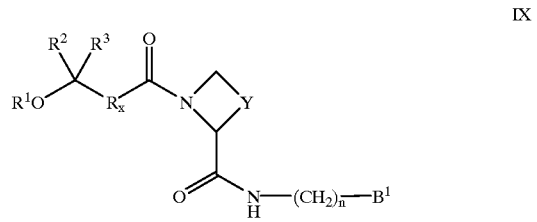

IX wherein $B^1$ represents a structural fragment of formula $IVa^1$, $IVb^1$ or $IVc^1$ IVa¹

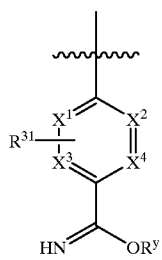

IVb¹

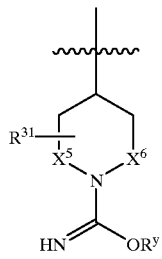

IVc¹

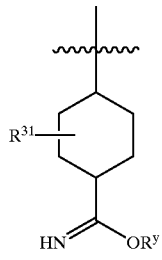

wherein R$^y$ represents C$_{1-4}$ alkyl and R$^1$, R$^2$, R$^3$, R$_x$, Y, n, X$^1$, X$^2$, X$^3$, X$^4$, X$^5$, X$^6$ and R$^{31}$ are as defined in claim 1, with ammonia gas;

(d) for compounds of formula I in which B represents a structural fragment of formula IVa, IVb or IVc, reduction of a compound of formula X,

X

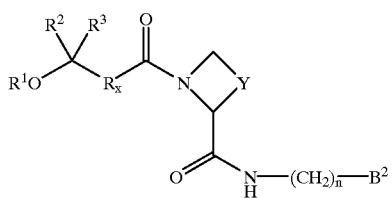

wherein B$^2$ represents a structural fragment of formula IVa$^2$, IVb$^2$ or IVc$^2$ IVa²

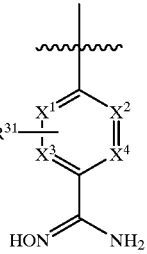

IVb²

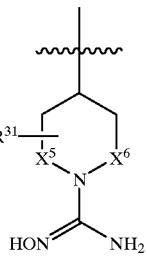

IVc²

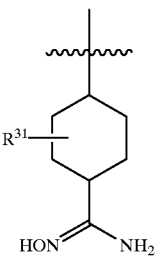

and R$^1$, R$^2$, R$^3$, R$_x$, Y, n, X$^1$, X$^2$, X$^3$, X$^4$, X$^5$, X$^6$ and R$^{31}$ are as defined in claim 1; or (e) for compounds of formula I wherein X$^1$, X$^2$, X$^3$, X$^4$, X$^7$, X$^8$ and/or X$^9$ represent N—O, oxidation of a corresponding compound of formula I in which X$^1$, X$^2$, X$^3$, X$^4$, X$^7$, X$^8$ and/or X$^9$ (as appropriate) represent N.

* * * * *

UNITED STATES PATENT AND TRADEMARK OFFICE
CERTIFICATE OF CORRECTION

PATENT NO. : 6,337,394 B2
DATED : January 8, 2002
INVENTOR(S) : Karlsson et al.

It is certified that error appears in the above-identified patent and that said Letters Patent is hereby corrected as shown below:

<u>Title page,</u>
Item [73], in the designation of the assignee, delete "Sodertalje" and insert
-- Södertälje -- therefor.

<u>Column 5,</u>
Line 38, delete "fragment for formula" and insert -- fragment of formula -- therefor.
Line 40, delete "formula or IVb" and insert -- formula IVb -- therefor.
Line 41, delete "formula or IVc" and insert -- formula IVc -- therefor.

<u>Column 13,</u>
Line 34, delete "$R^-$" and insert -- $R^{31}$ -- therefor.

<u>Column 14,</u>
Line 14, delete "$R^cC(O)-O-C(O)R^c$" and insert -- $R^cOC(O)-O-C(O)OR^c$ --.

<u>Column 19,</u>
Line 64, delete "which" and insert -- with -- therefor.

<u>Column 26,</u>
Lines 29 to 30, delete "fragment for formula" and insert -- fragment of formula -- therefor.
Lines 31 to 32, delete "formula or IVb" and insert -- formula IVb -- therefor.
Line 32, delete "formula or IVc" and insert -- formula IVc -- therefor.
Line 67, delete "or IV" and insert -- or IVh -- therefor.

<u>Column 27,</u>
Line 53, delete "R_hd x" and insert -- $R_x$ -- therefor.

Signed and Sealed this

Twenty-ninth Day of October, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.     : 6,337,394 B2
DATED          : January 8, 2002
INVENTOR(S)    : Karlsson et al.

It is certified that error appears in the above-identified patent and that said Letters Patent is hereby corrected as shown below:

<u>Title page,</u>
Item [75], Inventors, delete "Lindome" and insert -- Mölndal -- therefor.

Signed and Sealed this

Twenty-third Day of September, 2003

JAMES E. ROGAN
*Director of the United States Patent and Trademark Office*